United States Patent
Prisco et al.

(10) Patent No.: US 8,644,988 B2
(45) Date of Patent: Feb. 4, 2014

(54) DRIVE FORCE CONTROL IN MEDICAL INSTRUMENT PROVIDING POSITION MEASUREMENTS

(75) Inventors: Giuseppe Maria Prisco, Mountain View, CA (US); Samuel Kwok Wai Au, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 563 days.

(21) Appl. No.: 12/780,417

(22) Filed: May 14, 2010

(65) Prior Publication Data
US 2011/0282491 A1 Nov. 17, 2011

(51) Int. Cl.
*A61B 19/00* (2006.01)
*A61M 25/08* (2006.01)

(52) U.S. Cl.
USPC ............ 700/245; 604/528; 606/130; 600/146

(58) Field of Classification Search
USPC ............... 600/106, 142–152; 604/528; 606/1, 606/130, 108; 700/245; 701/23; 901/1, 9
See application file for complete search history.

(56) References Cited

U.S. PATENT DOCUMENTS

| | | | |
|---|---|---|---|
| 4,068,156 A | | 1/1978 | Johnson et al. |
| 6,322,567 B1 * | | 11/2001 | Mittelstadt et al. ............ 606/130 |
| 6,817,974 B2 * | | 11/2004 | Cooper et al. ................. 600/142 |
| 7,930,065 B2 * | | 4/2011 | Larkin et al. .................. 700/245 |
| 2006/0084945 A1 | | 4/2006 | Moll et al. |
| 2007/0156019 A1 | | 7/2007 | Larkin et al. |
| 2007/0287992 A1 * | | 12/2007 | Diolaiti et al. ................... 606/1 |
| 2008/0065101 A1 * | | 3/2008 | Larkin ........................... 606/130 |
| 2008/0065110 A1 * | | 3/2008 | Duval et al. ................... 606/130 |
| 2008/0255505 A1 | | 10/2008 | Carlson et al. |
| 2009/0088774 A1 | | 4/2009 | Swarup et al. |
| 2009/0171374 A1 | | 7/2009 | Omori |
| 2009/0324160 A1 | | 12/2009 | Rogers et al. |
| 2009/0324161 A1 | | 12/2009 | Prisco |
| 2010/0082041 A1 * | | 4/2010 | Prisco ............................ 606/130 |
| 2010/0274087 A1 * | | 10/2010 | Diolaiti et al. ................ 600/118 |

FOREIGN PATENT DOCUMENTS

EP 2108327 A1 10/2009

OTHER PUBLICATIONS

Vertut, Jean and Phillipe Coiffet, *Robot Technology: Teleoperation and Robotics Evolution and Development*, English translation Prentice-Hall, Inc., Inglewood Cliffs, NJ, USA 1986, vol. 3A, 332 pages.
PCT/US2011/035614 International Search Report and Written Opinion of the International Searching Authority, mailed Aug. 4, 2011, 10 pages.

* cited by examiner

Primary Examiner — Ruth Ilan

(57) ABSTRACT

Control systems and methods for a remote joint use position measurements to determine and control the force that an actuator applies to the joint through a linkage. The use of force and feedback allows control of a medical instrument having a linkage that provides non-negligible compliance between the joint and a proximal actuator and particularly allows precise instrument operation even when the position of the distal joint cannot be directly related to the proximal motor position.

29 Claims, 3 Drawing Sheets

DRIVE FORCE CONTROL IN MEDICAL INSTRUMENT PROVIDING POSITION MEASUREMENTS

BACKGROUND

Minimally invasive medical procedures often employ instruments that are controlled with the aid of a computer or through a computer interface. FIG. 1, for example, shows a robotically controlled instrument 100 having a structure that is simplified to illustrate basic working principles of some current robotically controlled medical instruments. (As used herein, the terms "robot" or "robotically" and the like include teleoperation or telerobotic aspects.) Instrument 100 includes a tool or end effector 110 at the distal end of an elongated shaft or main tube 120. In the illustrated example, end effector 110 is a jawed tool such as forceps or scissors having separate jaws 112 and 114, and at least jaw 112 is movable to open or close relative to jaw 114. In use during a medical procedure, end effector 110 on the distal end of main tube 120 may be inserted through a small incision in a patient and positioned at a work site within the patient. Jaws 112 may then be opened and closed, for example, during performance of surgical task, and accordingly must be precisely controlled to perform only the desired movements. A practical medical instrument will, in general, require many degrees of freedom of movement in addition to opening and closing of jaws 112 and 114 in order to perform a medical procedure.

The proximal end of main tube 120 attaches to a transmission or drive mechanism 130 that is sometimes referred to as backend mechanism 130. Tendons 122 and 124, which may be stranded cables, rods, tubes, or combinations of such structures, run from backend mechanism 130 through main tube 120 and attach to end effector 110. A typical surgical instrument would also include additional tendons (not shown) that connects backend mechanism 130 to other actuated members or joints of end effector 110, a wrist mechanism (not shown), or even actuated vertebrae in main tube 120, so that backend mechanism 130 can manipulate the tendons to operate end effector 110 and/or other actuated elements of instrument 100. FIG. 1 illustrates jaw 112 as having a pin joint structure 116 that provides a single degree of freedom for movement of jaw 112. Two tendons 122 and 124 are attached to jaw 112 and to a pulley 132 in backend mechanism 130, so that rotations of pulley 132 cause jaw 112 to rotate.

Pulley 132 is attached to a drive motor 140, which may be at the end of a mechanical arm (not shown), and a control system 150 electrically controls drive motor 140. Control system 150 generally includes a computing system along with suitable software, firmware, and peripheral hardware. Among other functions, control system 150 can implement an interface that provides a surgeon or other system operator with an image (e.g., a stereoscopic view) of the work site and end effector 110, and the interface also provides a control device that the surgeon can manipulate to control the movement of end effector 110. The software or firmware needed for interpretation of user manipulations of the control device and for generation of the motor signals that cause the corresponding movement of jaw 112 are generally complex in a real robotic medical instrument. To consider one part of the control task, the generation of the control signals for drive motor 140 commonly employs the relationship between the angle or position of jaw 112 and the angle or position of drive motor 140 or pulley 132 in backend mechanism 130. If the tendons 122 and 124 are extremely rigid (e.g., if stretching of tendons is negligible), control system 150 can use a direct relationship between the angular position of drive motor 140 and the angular position of jaw 112 as defined by the geometry of instrument 100 in determining the control signals needed to move jaw 112 as a surgeon directs. Minor stretching of tendons 122 and 124, for example, under a working load, can be handled by some mathematical models relating motor position to effector position. However, if the mechanical structure including end effector 110, tendons 122 and 124, and backend mechanism 130 has a high degree of compliance, a relationship between the angular position of motor 140 (or pulley 132) and the angular position of jaw 112 may be difficult or impossible to accurately model. Accordingly, such systems require control processes that do not rely on a fixed relationship between the applied actuator control signals and the position of the actuated elements.

SUMMARY

In accordance with an aspect of the invention, control systems and methods use distal position feedback to determine and control the forces that one or more proximal actuators apply to the joint via mechanical linkages. The use of force control and distal feedback allows robotic control of a medical instrument having a mechanical linkage that has non-negligible compliance between the joint and the proximal actuators and particularly allows precise instrument operation even when the position of the distal joint cannot be directly inferred from the proximal motor position. Additionally, use of force control also allows active control of a remote joint in a medical instrument to provide a desired joint stiffness. For example, stiffness of the joint can be kept within a range required to achieve a medical function such as manipulating the tissue or can be made more compliant when inserting the instrument into a small lumen to avoid damaging the surrounding tissues. Further, through use of force control and distal feedback, a control system can provide both position control and stiffness control of a remote joint of a medical instrument independently of the position of the actuator.

One specific embodiment of the invention is a medical system including an actuator, a joint; a linkage, a sensor, and a control system. The linkage has a first end attached to the joint and a second end mechanically coupled to the actuator to allow the transmission of a force for articulation of the joint. The sensor is coupled to measure a position of the joint; and the control system coupled to receive position measurements. The control system uses the position measurements to determine how to regulate an actuator force transmitted from the actuator to the linkage.

Another specific embodiment of the invention is a method for controlling a joint of a medical instrument. The method generally includes: measuring a position of a joint; receiving a command indicating a desired position of the joint; determining an actuator force that depends on the measured position and the desired position of the joint but is independent of a position of the actuator, and operating an actuator to apply the actuator force to a linkage that is coupled to the joint. Determining the actuator force can include calculating a value of a function that depends on the position joint and the desired position of the joint.

BRIEF DESCRIPTION OF THE DRAWINGS

Use of the same reference symbols in different figures indicates similar or identical items.

DETAILED DESCRIPTION

In accordance with an aspect of the invention, a remote joint in a medical instrument can be controlled via a linkage that does not provided a fixed relationship between actuator position and joint position. In particular, the actions of a system operator (e.g., a surgeon) can indicate a currently desired position and velocity of the remote joint, while a sensor measures the actual position of the remote joint. A force, tension, or torque can then be calculated using the desired and measured positions and applied through the linkage to move the remote joint from its actual position toward its desired position. (In general, the force or tension in a medical instrument is proportional to a torque with the proportionality defined by a fixed factor, i.e., the moment arm, which is set by the mechanical or geometric properties of the instrument, so that calculation of any one of the force, tension, or torque will indicate the values of the other two.) The calculation of the force that an actuator applies can be corrected or adapted if prior calculations of applied force resulted in the joint overshooting or failing to reach a desired position.

Figure 2:
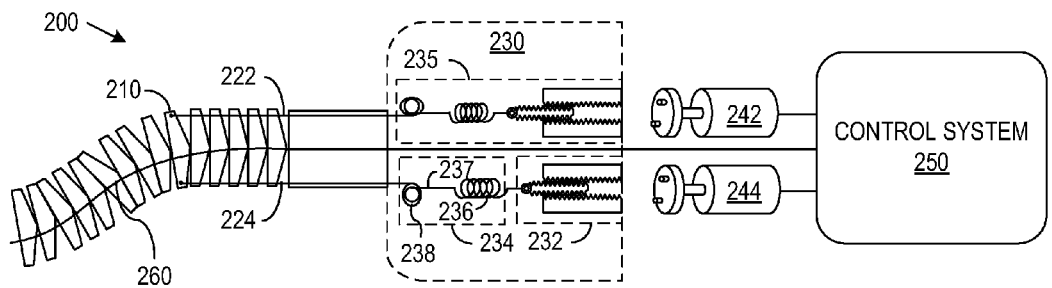
FIG. 2 is a block diagram of a medical instrument in which force control processes in accordance with an embodiment of the invention can be employed with a compliant drive.

FIG. 2 illustrates a portion of a compliant medical instrument 200 having a drive linkage such as described by U.S. Pat. App. Pub. No. 2010/0331820, entitled "Compliant Surgical Device," which is hereby incorporated by reference in its entirety. Instrument 200 includes a jointed element 210 that is manipulated through control of the respective tensions in tendons 222 and 224. In general, instrument 200 may contain many mechanical joints similar to jointed element 210, and each joint may be controlled using tendons similar to tendons 222 and 224. In an exemplary embodiment, instrument 200 is an entry guide that can be manipulated to follow a natural lumen within a patient. An entry guide would typically include a flexible outer sheath (not shown) that surrounds vertebrae (including element 210) and provide one or more central lumens through which other medical instruments can be inserted for access to a work site. Compliance is particularly desirable in entry guides to prevent an action or reaction of the entry guide from harming surrounding tissue that may move or press against the entry guide. However, other types of medical instruments may also benefit from compliant drive mechanisms of the type illustrated in FIG. 2.

Instrument 200 includes a backend mechanism 230 that with tendons 222 and 224 provides a compliant linkage connecting to jointed element 210 to drive motors 242 and 244. In particular, backend mechanism 230 includes spring systems 235 attached to tendons 222 and 224 and drive motors 242 and 244. Each spring system 235 in FIG. 2 includes a mechanical drive system 232 and a constant force spring 234. Each drive system 232 couples a motor 242 or 244 and converts rotational motion of the drive motor 242 or 244 into linear motion that changes the constant force applied by the associated constant force spring 234 to tendon 222 or 224. In the illustrated embodiment, each constant force spring 234 includes a conventional Hooke's law spring 236 and a cam 238. Each spring 236 connects to an associated drive system 232 so that the linear motion of drive system 232 moves a proximal end of the spring 236. Each cam 238 has a first guide surface on which a cable 237 attached to the distal end of the associated spring 236 attaches and rides and a second guide surface on which a portion of tendon 222 or 224 attaches and rides. The guide surfaces of each cam 238 generally provide different moment arms for the action of the attached cable 237 and the attached tendon 222 or 224 and are shaped so that the tension in tendon 222 or 224 remains constant as the paying out or hauling in of a length of tendon 220 or 224 changes the force applied by the attached spring 236. Each surface of each cam 238 may be a spiral surface that extends for one or more revolutions in order to provide the desired range of movement of the tendon 222 and 224 while maintaining a constant tension in tendon 222 or 224.

Each drive system 232 controls the position of the proximal end of the corresponding spring 236 and thereby influences the amount of baseline stretch in the corresponding spring 236 and the tension in the attached tendon 222 or 224. In operation, if a drive system 232 in a spring system 235 pulls on the attached spring 236, the spring 236 begins to stretch, and if the element 210 and tendons 222 and 224 attached to the spring system 235 are held fixed, the force that spring 236 applies to cam 238 increases and therefore the tension in the attached cable 222 or 224 increases. Accordingly, the tensions in tendons 222 and 224 depends linearly (in accordance with Hooke's law, the moment arms of cam 238, and the spring constant of spring 236) on movement of the proximal ends of respective springs 236, but each spring system 235 behaves asymmetrically, i.e., acts with constant force in response to external or distal forces that move tendon 222 or 224. Constant force spring 234 and drive system 232 can be alternatively implemented in a variety of ways such as those described further in above-referenced U.S. patent application Ser. No. 12/494,797.

Jointed element 210 has a single degree of freedom of motion (e.g., rotation about an axis) and generally moves when drive motor 242 or 244 rotates a drive system 232 to change the force applied by the attached constant force spring 238. However, this drive mechanism is compliant so that external forces can move element 210 without a corresponding rotation of drive system 232. As a result, there is no fixed relationship between the position or orientation of jointed element 210 and the position of drive system 232 or drive motor 242. In accordance with an aspect of the invention, control system 250 uses a sensor 260 to measure the orientation of element 210. Sensor 260 may be, for example, a shape sensor, which can sense the shape of the main tube along a length of instrument 200 including element 210. Some examples of shape sensors are described in U.S. Pat. App. Pub. No. US 2007/0156019 A1 (filed Jul. 20, 2006), entitled "Robotic Surgery System Including Position Sensors Using Fiber Bragg Gratings" by Larkin et al., and U.S. Pat. No.

7,720,322, entitled "Fiber optic shape sensor" by Giuseppe M. Prisco, both of which are incorporated herein by reference. However, any sensor capable of measuring an angular position of jointed element 210 could alternatively be used. A control process as described further below uses such measurements for calculation of applied forces needed to manipulate jointed element 210.

Instrument 200 has "backdriving" capability when backend mechanism 230 is detached from a motor pack, constant force springs 235 still keep tendons 222 and 224 from slacking and allow the distal portion of instrument to be manually arranged (or posed) without damaging backend mechanism 230 or creating slack in tendon 222 or 224. This "backdriving" capability is generally a desirable property of a surgical instrument, particularly an instrument with a flexible main tube that may be bent or manipulated during instrument insertion while the instrument is not under active control by control system 250. For example, instrument 200 can be manually posed, and the tendons within the main shaft do not experience undue tension or slack.

Figure 3A:
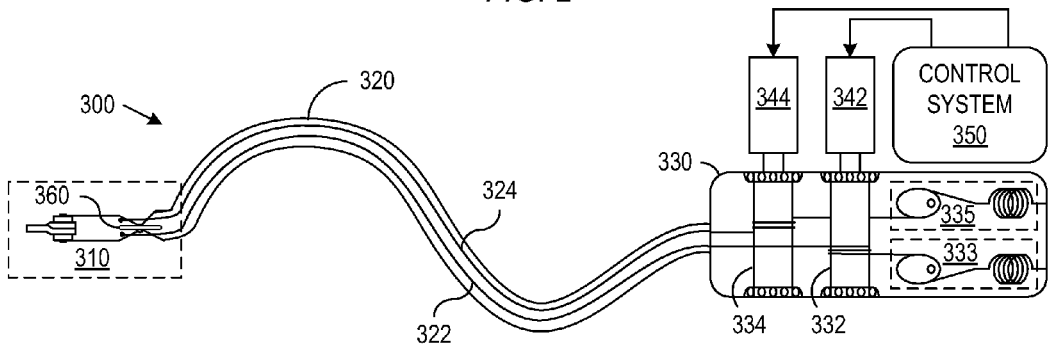
FIG. 3A is a block diagram of a medical instrument in which control processes in accordance with an embodiment of the invention can be applied with a drive linkage having minimum and maximum force transfer.

Another example of a compliant drive linkage for a joint in a medical instrument is illustrated in FIG. 3A. FIG. 3A shows an exemplary embodiment of a medical instrument 300 that uses an actuation process that permits a drive motor to freewheel or a drive tendon to slip relative to the drive motor during instrument operation as described in U.S. Pat. App. Pub No. 2010/0082041, entitled "Passive Preload and Capstan Drive for Surgical Instruments," which is hereby incorporated by reference in its entirety. Medical instrument 300 has an end effector 310 at the end of a main tube 320, and a backend mechanism 330 manipulates tendons 322 and 324, which run through main tube 320, to control a degree of freedom of motion of end effector 310. In the illustrated embodiment, tendons 322 and 324 attach to a mechanical member in end effector 310 such that tensions in tendons 322 and 324 tend to cause end effector 310 to rotate in opposite directions about a pivot joint structure.

Figure 3B:
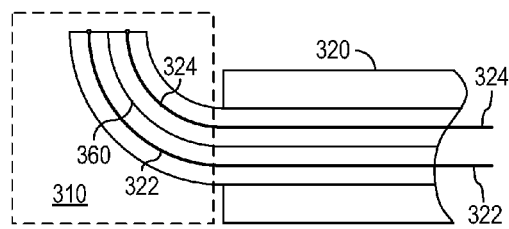
FIG. 3B shows an embodiment of the invention in which the joint controlled is continuously flexible structure.

The joint structure of FIG. 3A is only an example, and other joint mechanisms that provide a single degree of freedom of motion in response to tensions applied to a pair of tendons could be employed in alternative embodiments of the invention. FIG. 3B, for example, illustrates an embodiment in which joint 310 corresponds to a section of a catheter that is able to flex or bend in response to forces applied through tendons 322 and 324. The catheter joint may simply include an extrusion of a plastic material that bends in response to a differential in the tension in tendons 322 and 324. In this configuration, tendons 322 and 324 extend through lumens within the catheter and attach to the end of the catheter. Accordingly, the forces in tendons 322 and 324 can be used to bend the catheter, for example, to steer the catheter during insertion. In the embodiment of FIG. 3B, distal sensor 360 can measure the bend angle of the distal portion of the catheter to measure or compute the 'joint' angle and velocity. The backend and control architecture for catheter joint 310 of FIG. 3B can be identical to that of the embodiment of FIG. 3A, except that the measured joint angle and velocity can be converted to tendon position and velocity by multiplication of the distance between the actuator cable lumen and the center of the distal flexible portion.

Backend mechanism 330, which attaches to the proximal end of main tube 320, acts as a transmission that converts torques applied by drive motors 342 and 344 into tensions in respective tendons 322 and 324 and forces or torques applied to an actuated joint in end effector 310. In the illustrated embodiment, drive motors 342 and 344 can be direct drive electrical motors that directly couple to capstan 332 and 334 around which respective tendons 322 and 324 wrap. In particular, tendon 322 wraps for a set wrapping angle (that could be less than a full turn or as large as one or more turns) around the corresponding capstan 332 and has an end that is not affixed to capstan 332 but extends from the capstan 332 to a passive preload system 333. Similarly, tendon 324 wraps for a set wrapping angle around the corresponding capstan 334 and has an end extending from the capstan 334 to a passive preload system 335. Since tendons 322 and 324 are not required to be permanently attached to capstans 332 and 334, tendon 322 and 324 may be able to slip relative to capstans 332 and 334 and relative to the shaft of drive motors 342 and 344 that respectively couple to capstans 332 and 334.

The proximal end of tendons 322 and 324 attach to respective passive preload systems 333 and 335, each of which is implemented in FIG. 3A as a cam and a Hooke's law spring that together act as a constant force spring. Passive preload systems 333 and 335 are biased, so that systems 332 and 334 apply non-zero forces or tensions to tendons 322 and 324 throughout the range of motion of instrument 300. With this configuration, when capstans 332 and 334 are free to rotate, passive preload systems 333 and 335 control the tensions in tendons 322 and 324 and avoid slack in tendons 322 and 324 by pulling in or letting out the required lengths of tendons 322 and 324. When backend mechanism 330 is detached from motors 342 and 344, passive preload systems 333 and 335 still keep tendons 322 and 324 from slacking and allow end effector 310 and main tube 320 (when flexible) to be manually arranged (or posed) without damaging backend mechanism 330 or creating slack in tendon 322 or 324. Accordingly, instrument 300 also has "backdriving" capability similar to that described above for instrument 200 of FIG. 2.

End effector 310 can be operated using drive motors 342 and 344 under the active control of control system 350 and human input (e.g., master control input in a master-slave servo control system). For example, when motor 342 pulls on tendon 322, the motor torque is transferred as an applied tension in the distal portion of tendon 322. (A maximum tension that capstan 332 can apply to proximal portion of tendon 322 depends on a tension at which tendon 322 begins to slip relative to captain 332, but in general, the maximum tension actually used can be selected to prevent tendons 322 and 324 from slipping on capstans 332 and 334.) At the same time, when turning off the power to motor 344, allowing motor 344 and capstan 334 to freewheel, tendon 324 can be kept at its minimum tension that is the constant force that passive preload system 335 applies to proximal end of tendon 324 through the capstan 334. The larger tension in tendon 322 then tends to cause end effector 310 to rotate counterclockwise in FIG. 3A. Similarly, turning off power to motor 342 and powering motor 344 to apply force through tendon 324 to end effector 310 tends to cause end effector 310 to rotate clockwise in FIG. 3A. The ability of motor 342 and 344 to freewheel while tendons 322 and 324 are under tension and the acceptance of slippage of tendons 322 and 324 on capstans 332 and 334 do not permit control system 350 to rely on a fixed relationship between the angular positions of motor 340 and end effector 310. However, control system 350 can use a sensor 360 to measure the angular position end effector 310 relative to the joint actuated through tendons 322 and 324.

Figure 1:
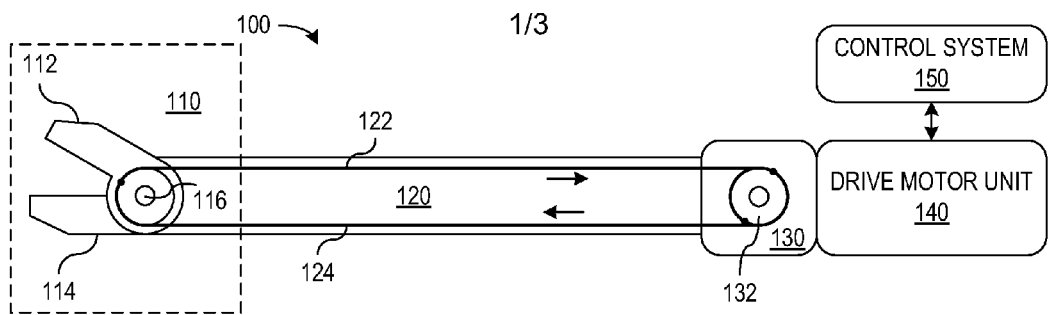
FIG. 1 illustrates features of a known robotically controlled medical instrument.
Figure 4:
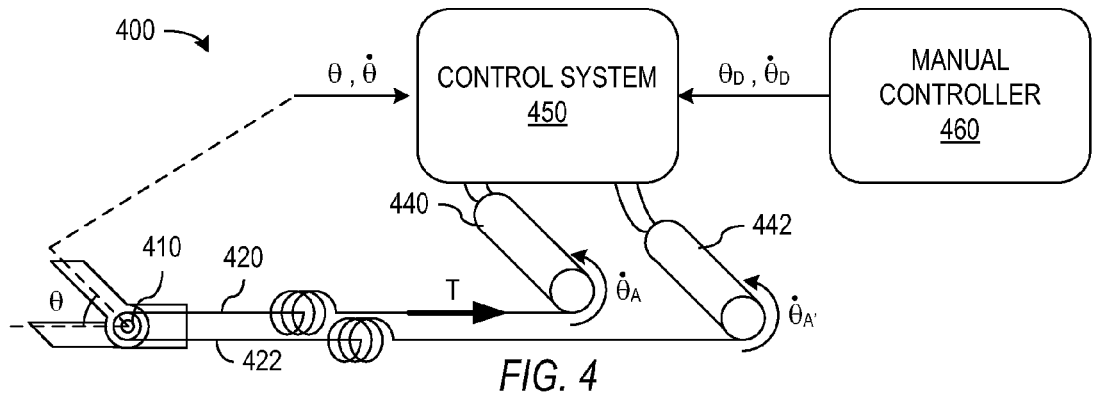
FIG. 4 schematically illustrates a robotic medical system and particularly shows quantities used in the control of a remote joint connected to an actuator through a compliant mechanical link.

The instruments of FIGS. 2 and 3A linkages between actuators and joints that are actuated provide compliance that is desirable, particularly for instruments with a flexible main tube. However, linkages with compliance may also occur in more traditional instruments. For example, the known instrument of FIG. 1 may use sheathed or Bowden cables in sections of the instrument that bend and rod elements in straight sections. The rod elements can reduce stretching that interferes with the direct relationship of actuator and joint positions. However, it may be desirable in some applications to use tendons of more flexible material (e.g., polymer tendons where electrical insulation or minimal friction is desired), but such tendons may introduce an unacceptable amount of stretch for control processes relying on a direct relationship between actuator and joint position. In accordance with an aspect of the current invention, control processes for the medical instruments of FIGS. 2 and 3A or instruments that otherwise have compliant linkages can employ remote measurements of the position of a mechanical joint to determine a tension to be applied to drive the mechanical joint. FIG. 4 schematically shows a generalization of a medical instrument 400 having a mechanical joint 410 having a degree of freedom of motion corresponding to an angle or position θ.

Joint 410 in general can be any mechanical means that provides a single degree of freedom of motion between two sections of a medical instrument. In one embodiment, joint 410 can be a rotary mechanism that allows two rigid link members to rotate around a joint axis. In another embodiment, the rotation between the two rigid links is not around a fixed axis. In another embodiment, the rotation between the two rigid links is realized by a bending flexible section that joins the links. In another embodiment, joint 410 is a bending section that is flexed by actuation linkages 420 and 422 thus changing the relative angle between two adjacent sections of a continuously flexible member such as a catheter.

The term position is used broadly herein to include the Cartesian position, angular position, or other indication of the configuration of a degree of freedom of a mechanical system. A sensor (not shown) measures position θ at the remote joint 410 and provides measured position θ to a control system 450, for example, through a signal wire (not shown) extending from the sensor at the distal end of instrument 400, through the main tube (not shown) of instrument 400 to control system 450 at the proximal end of the instrument. The sensor may additionally measure a velocity $\dot{\theta}$ for the movement of joint 410, or velocity $\dot{\theta}$ may be inferred from two or more measurements of position θ.

Joint 410 is connected through a compliant linkage 420 to an actuator 440, so that joint 410 is remote from the actuator, e.g., joint 410 may be at a distal end of the instrument while actuator 440 is at the proximal end of the instrument. In the illustrated embodiment, compliant linkage 420 connects joint 410 so that a tension T applied by actuator 440 to linkage 420 tends to rotate joint 410 in a clockwise direction. However, linkage 420 may be (but is not required to be) so compliant that a direct relationship between the position of joint 410 and the position of actuator 440 would not be accurate enough for control of joint 410. For example, linkage 420 may stretch, so that between a minimum and a maximum of applied tension T, linkage 420 the difference in the effective length of linkage 420 may correspond to 45° of joint articulation. In contrast, a typical medical device allows for stretching that corresponds to no more than a few degrees of joint articulation in order to be able to accurately model the position of the joint based on actuator position. It should be understood that in the general case compliance is not limited to a simple Hooke's law stretching of a spring structure. Compliant linkage 420 may include, for example, tendon 222 and at least a portion of backend mechanism 230 in the embodiment of FIG. 2 or tendon 322 and at least a portion of backend mechanism 330 in the embodiment of FIG. 3A. In general, the response of linkage 420 to a tension T applied at a proximal end of linkage 420 and to external forces applied to joint 410 on along the length of linkage 420 may be difficult to model.

Actuator 440, which can include drive motor 242 or 342 of FIG. 2 or 3A, applies tension T to the proximal end of linkage 420 and through linkage 420 applies force or torque to joint 410, but other forces and torques are also applied to joint 410. In particular, one or more other linkages 420 may be connected to joint 410 and collectively apply a net tension or force that tends to cause joint 410 to rotate. In the illustrated embodiment of FIG. 4, a single linkage 422 is connected to joint 410 and to a drive motor 442, so that tension in linkage 422 tends to oppose applied tension T and rotate joint 410 counterclockwise in FIG. 4. The additional linkage 422 or linkages may be the same as linkage 420, other than a difference in where the linkages 422 connect to joint 410.

Control system 450 can be a general purpose computer executing a program or a circuit wired to generate a drive signal that controls a tension T that actuator 440 applies to compliant linkage 420. When actuator 440 is an electrical motor, the drive signal may be a drive voltage or current that controls the torque output from actuator 440, and tension T is equal to the motor torque divided by the effective moment arm at which tension T is applied to linkage 420. As described further below, control system 450 can calculate the magnitude of tension T or the motor torque using a desired position $\theta_D$, a desired velocity $\dot{\theta}_D$ for joint 410, and one or more measurements of position θ for joint 410 at the current and prior times. A user (e.g., a surgeon controlling system 400) can provide desired position $\theta_D$ and velocity $\dot{\theta}_D$ by manipulating a controller 460. The exact configuration of controller 460 is not critical to present invention except that controller 460 is able to provide signals from which values for the desired position $\dot{\theta}_D$ and velocity $\dot{\theta}_D$ can be determined. Manual controllers suitable for complex medical instruments generally provide signals that indicate many simultaneous instructions for movements of the medical instrument, and such movements may involve multiple joints in the instrument. Suitable manipulators for use as controller 460 are provided, for example, in the master controller of the da Vinci Surgical System available from Intuitive Surgical, Inc.

The tension T needed to move joint 410 from its current measured position θ to desired position $\theta_D$ in a time interval Δt in general will depend on many factors including: the effective inertia of joint 410 that resists applied tension T; the inertia of actuator 440 which applies tension T, any other linkages coupled to joint 410 and applying a net effective force; external forces applied to joint 410; internal and external frictional forces that oppose actuation of joint 410 or movement of linkage; the current velocity $\dot{\theta}$ of joint 410; and internal and external damping forces. Many of these factors may vary depending on the working environment of instrument 400 and may be difficult to measure or model. However, models can be developed based on system mechanics or empirically for a particular joint in a medical instrument. In one specific embodiment, control system 450 determines the tension T from the distal joint errors $(\theta_D-\theta)$ and $(\dot{\theta}_D-\dot{\theta})$, which are respectively the difference between the measured and desired positions of joint 410 and the difference between measured and desired velocities of joint 410. In particular, an applied tension T that increases with errors $(\theta_D-\theta)$ and $(\dot{\theta}_D-\dot{\theta})$ will tend to cause the position of joint 410 to converge on the desired position.

Figure 5:
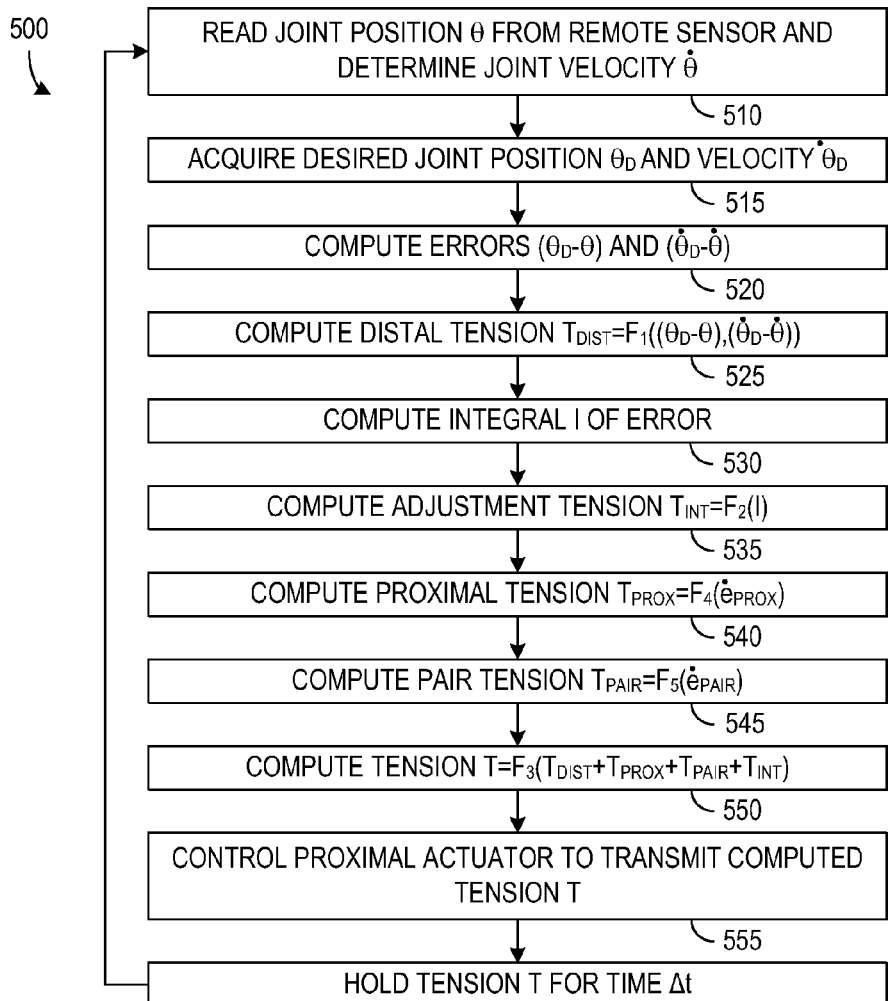
FIG. 5 is a flow diagram of a control process in accordance with an embodiment of the invention.

FIG. 5 is a flow diagram of a process 500 for controlling a medical instrument having the basic structure of system 400 of FIG. 4. Process 500 begins in step 510 by reading a current value of position θ of joint 410 and determining a current value for the joint velocity $\dot{\theta}$. The velocity can be directly measured or determined or approximated in a well known manner using the current position θ, a prior position θ', a time interval Δt between measurements, for example, under the assumption of constant velocity (e.g., $\dot{\theta}=(\theta-\theta')/\Delta t$) or under the assumption of constant acceleration given a prior determination of velocity. Step 515 then acquires a desired position $\theta_D$ and a desired velocity $\dot{\theta}_D$ for joint 410, and step 520 computes a difference or error ($\theta_D-\theta$) between the measured and desired positions and a difference or error ($\dot{\theta}_D-\dot{\theta}$) between the measured and desired velocities.

The position and velocity error computed in step 520 can be used to determine tension T required for joint 410 to reach the desired position $\theta_D$. In the embodiment of FIG. 5, applied tension T may include multiple contributions, and the primary contribution is a distal tension $T_{DIST}$, which is determined as a function $F_1$ of position error ($\theta_D-\theta$) and velocity error ($\dot{\theta}_D-\dot{\theta}$). Distal tension $T_{DIST}$ is independent of the position of the actuator, e.g., of the angle of the motor shaft, which allows determination of distal tension $T_{DIST}$ even when there is no direct relationship between the position of joint 410 and the position of actuator 440. In one particular embodiment, the function $F_1$ is of the form Equation 1, where g1 and g2 are gain factors, C is a constant or geometry dependent parameter, and $T_{sign}$ is the linkage sign. Sign $T_{sign}$ is associated with movement of joint 410 produced by tension in linkage 420 and may, for example, be positive (e.g., +1) if tension T in linkage 420 tends to increase the position coordinate θ and negative (e.g., −1) if tension T in linkage 420 tends to decrease the position coordinate θ. In another embodiment, function $F_1$ imposes a lower bound on the force, for instance, in order for the force to be always positive. The parameter C can be a constant selected according to known or modeled forces applied to joint 410 by other portions of the system. For example, parameter C may be a constant selected to balance the torque caused by other linkages applying force to joint 410 or may account for expected friction or external forces. However, parameter C is not required to strictly be a constant but could include non-constant terms that compensate for properties such gravity or mechanism stiffness that can be effectively modeled, and accordingly, C may depend on the measured joint position or velocity. The gain factors g1 and g2 can be selected according to the desired stiffness of joint 410. In particular, when joint 410 is used as a static grip, the net gripping force or torque applied to tissue depends on the term g1($\theta_D-\theta$) of Equation 1. In general, gain factors g1 and g2 and constant C can be selected according to the desired stiffness or responsiveness of joint 410 or according to an accumulation of error. For example, when inserting the instrument 400 to follow a natural lumen within a patient, the gain factor g1 can be set to a low value to make joint 410 behave gently and prevent joint 410 from harming surrounding tissue. After the insertion, the gain factor g1 can be set to a higher value that allows the surgeon to perform precise surgical task with the instrument.

$$F_1 = T_{sign} * (g1(\theta_D-\theta) + g2(\dot{\theta}_D-\dot{\theta}) + C) \quad \text{Equation 1}$$

The term g1($\theta_D-\theta$)+g2($\dot{\theta}_D-\dot{\theta}$)+C of Equation 1 can be used to approximately determine the torque or force currently required at joint 410 to rotate joint 410 to reach the desired position $\theta_D$ using linkage 420 in a given time Δt. The torque and force are related in that the torque is the product of the force and an effective movement arm R, which is defined by the perpendicular distance between the connection of linkage 420 to joint 410 and the rotation axis of joint 410. The effective movement arm R can either be absorbed into gain factors g1 and g2 and constant C or used to convert a calculated distal tension $T_{DIST}$ into a calculated torque.

Distal tension $T_{DIST}$, with the proper choice of function $F_1$, e.g., proper selection of parameters g1, g2, and C in Equation 1, can approximate the force that actuator 440 is required to apply to move joint 410 in a manner that is responsive to manipulations by a human operator of master controller 260. However, optional corrections are provided by steps 530, 535, 540, and 545 under some conditions. In particular, optional steps 530 and 535 respectively compute a saturated sum or integral I of the position error ($\theta_D-\theta$) and calculate an integral tension $T_{INT}$. The integral tension $T_{INT}$, which may be positive, zero, or negative, can be added to distal tension $T_{DIST}$, which was calculated in step 525. Integral tension $T_{INT}$ is calculated as a function $F_2$ of saturated integral I and may simply be the product of integral I and a gain factor. The saturated integral I calculated in step 530 can simply be the sum for the past N intervals of position errors ($\theta_D-\theta$) or differences ($\theta_{D,i}-\theta_{i-1}$) between the measured position at the end of the interval and the desired position that was to be achieved. The number N of intervals involved in the sum may be limited or not, and integral I may be saturated in that the magnitude of the integral is not permitted to exceed a maximum saturation value. The saturation value would generally be selected to cap the maximum or minimum value of integral tension $T_{INT}$. However, the minimum and maximum values of integral tension $T_{INT}$ can alternatively be capped when calculating the value of function $F_2$.

Figure 6:
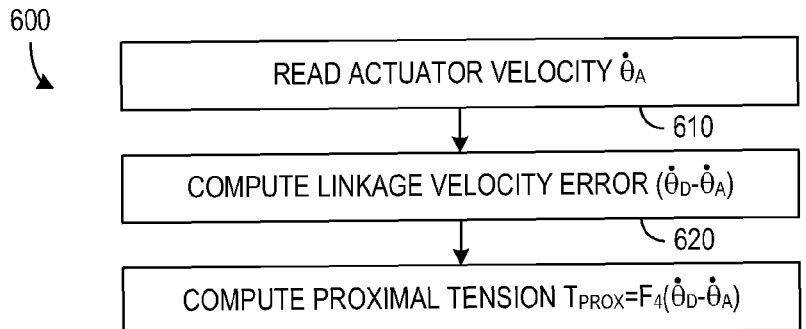
FIG. 6 is a flow diagram of a process for determining a tension contribution associated with a difference between an actuator velocity and a joint velocity.

Optional step 540 computes another adjustment referred to herein as proximal tension $T_{PROX}$, which may be positive, zero, or negative. Proximal tension $T_{PROX}$ can be added to distal tension TDIST, which was calculated in step 525. FIG. 6 is a flow diagram of a process 600 for computing proximal tension $T_{PROX}$. Process 600 begins in step 610 by reading a current value of a velocity $\dot{\theta}_A$ of actuator 440. Velocity $\dot{\theta}_A$ can be measured by a standard tachometer that attaches at the base of actuator 440. To improve computational efficiency, step 610 can also be scheduled to run between Steps 510 and 515 of FIG. 5. Step 620 then computes the proximal linkage velocity difference or error $\dot{e}_{PROX}$, which is defined as the difference or error between a desired linkage velocity computed based on desired velocity $\dot{\theta}_D$ of joint 410 and the current linkage velocity computed based on the current actuator velocity $\dot{\theta}_A$. In one particular embodiment, the desired linkage velocity can be the product of the effective moment arm R, linkage sign $T_{sign}$, and desired velocity $\dot{\theta}_D$ of joint 410, while the current linkage velocity can be the product of an effective moment arm of the actuator 440 and actuator velocity $\dot{\theta}_A$. In the embodiment of FIG. 6, proximal tension $T_{PROX}$ is determined as a function $F_4$ of proximal linkage velocity error $\dot{e}_{PROX}$. In one particular embodiment, the function $F_4$ may simply be the product of proximal linkage velocity error $\dot{e}_{PROX}$ and a gain factor. The gain factor can be selected to provide an additional dampening effect to the linkage 420.

Figure 7:
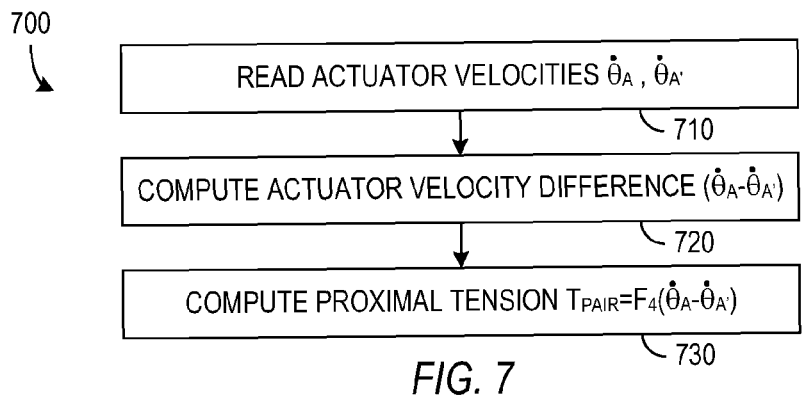
FIG. 7 is a flow diagram of a process for determining a tension contribution associated with the difference between the velocities of two actuators manipulating the same joint.

Optional step 545 of FIG. 5 computes a pair tension $T_{PAIR}$, which may be positive, zero, or negative adjustment to distal tension $T_{DIST}$, which was calculated in step 525. FIG. 7 is a flow diagram of a process 700 for computing the pair tension $T_{PAIR}$. Process 700 begins in step 710 by reading a current value of velocity $\dot{\theta}_A$ of actuator 440 and velocity values of all other actuators associated with joint 410. In the system of FIG. 4, there are two actuators 440 and 442 coupled to joint 410 and two actuator velocities $\dot{\theta}_A$ and $\dot{\theta}_{A'}$. Step 710 can be scheduled to run between steps 510 and 515 of FIG. 5 to improve computational efficiency. Step 620 then computes a pair linkage velocity difference or error $\dot{e}_{PAIR}$, which can defined as the difference or error between the current linkage velocities $\dot{\theta}_A$ and $\dot{\theta}_{A'}$ of the actuators 440 and 442 associated to joint 410, when actuators 440 and 442 are substantially identical, e.g., have the same effective moment arms for operation on respective linkages 420 and 422. In one particular embodiment, the current linkage velocity error $\dot{e}_{PAIR}$ can be the product of the difference $(\dot{\theta}_A - \dot{\theta}_{A'})$ and the effective moment arm of actuators 440 and 442. In the embodiment of FIG. 7, pair tension $T_{PAIR}$ is determined as a function $F_5$ of pair linkage velocity error $\dot{e}_{PAIR}$. In one particular embodiment, the function $F_5$ may simply be the product of pair linkage velocity error $\dot{e}_{PAIR}$ and a gain factor. The gain factor can be selected to provide additional dampening effect to the linkage 420.

Figure 8:
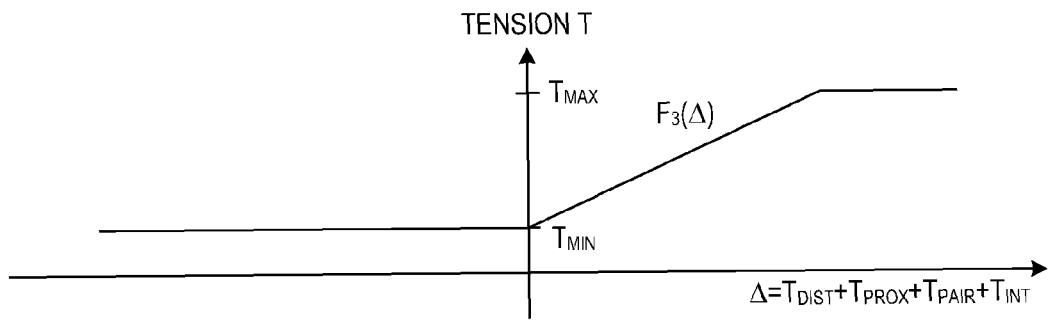
FIG. 8 illustrates the force function controlling a maximum and minimum applied tension.

Tension T is determined in step 550 of FIG. 5 as a function $F_3$ of sum of distal tension $T_{DIST}$, proximal tension $T_{PROX}$, pair tension $T_{PAIR}$, and integral tension $T_{INT}$. In the embodiment of FIG. 8, function $F_3$ limits the maximum and minimum values of tension T. Maximum tension $T_{MAX}$ and minimum tension $T_{MIN}$ can be set in the programming of control system 450 (e.g., in software). However, compliant linkage may itself have a minimum or maximum tension. For example, a linkage illustrated in FIG. 3A has a minimum tension $T_{MIN}$ controlled by the setting of preload system 333 or 335 when motor/actuator 342 or 344 is freewheeling and a maximum tension $T_{MAX}$ resulting from slipping when the torque of the couple motor 342 or 344 exceeds the point when the tendon 322 or 324 slips on capstan 332 or 334. In general, it is desirable to have maximum tension $T_{MAX}$ set by both hardware and software. In particular, maximum tension $T_{MAX}$ should be set to avoid damage to the instrument resulting from large forces, and tension $T_{MIN}$ should be set to ensure that tendons in the linkage do not slack and become derailed or tangled.

Step 555 of FIG. 5 generates a control signal that causes actuator 440 to apply tension T calculated in step 550. For example, the control signal when actuator 440 is a direct drive electrical motor may be a drive current that is controlled to be proportional to calculated tension T. Control system 450 in step 560 causes actuator 440 to apply and hold the calculate tension T for a time interval $\Delta t$, during which time, joint 410 moves toward the current desired position $\theta_D$. When changing the tension T, the application of the full tension T will be delayed by a time depending on the inertia of actuator 440. Preferably, the inertia of actuator 440 is relatively small for rapid response. For example, the inertia of a drive motor acting as actuator 440 would preferably be less than five times the inertia of joint 410. After time $\Delta t$, process 500 branches back to step 510 to repeat measurement of the joint position, acquisition of the target position and velocity, and calculation of the tension T to be applied during the next time interval. In general, time $\Delta t$ should be small enough to provide motion that appears to be smooth to the operator of the instrument and which does not cause undesirable vibrations in the instrument. For example, calculating and setting tension T two hundred and fifty times per second or more will provide movement that appears smooth to the human eye and will provide instrument operation that is responsive to human commands, e.g., to human manipulation of controller 460. Use of the errors in the calculation of the tension T will in general cause joint 410 to converge on the desired positions with or without the computation of integral tension $T_{INT}$ and without detailed modeling or measurement of the instrument or the external environment. However, as described above, parameters such as gains g1 and g2 used in calculating the applied tension T can be tuned for specific instruments and further tuned in use to compensate for changes in the external environment of the instrument.

The tension that actuator 442 applies to linkage 422 can also be controlled using control process 500 of FIG. 5, and parameters use in process 500 for actuator 442 and linkage 422 can be the same or different from those used for actuator 440 and linkage 420 based on the similarities and differences of actuator 442 and linkage 422 when compared to actuator 440 and linkage 420. In particular, the sign value $T_{sign}$ for actuator 442 in the configuration of FIG. 4 will be opposite to the sign value $T_{sign}$ for actuator 440 because linkages 422 and 420 connect to rotate joint 410 in opposite directions. As a result, the primary tension contribution $T_{DIST}$ calculated in step 525 will typically be negative for one actuator 440 or 442. Step 550, which calculates the applied tension T, can set a negative tension sum $T_{DIST} + T_{PROX} + T_{PAIR} + T_{INT}$ to the minimum tension $T_{MIN}$ as shown in FIG. 8. Accordingly, parameters, e.g., constant C, for the calculation of distal tension $T_{DIST}$ in step 525 can generally be selected based on the assumption that the other actuator will apply the minimum tension $T_{MIN}$.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A medical system including:
   an actuator;
   a joint;
   a linkage having a first end attached to the joint and a second end mechanically coupled to the actuator to allow the transmission of a force for articulation of the joint;
   a sensor coupled to measure a position of the joint; and
   a control system coupled to receive position measurements from the sensor and to use the position measurements to select an actuator force transmitted from the actuator to the linkage to thereby control the position of the joint.

2. The system of claim 1, wherein the joint is a mechanism selected from a group consisting of a rotary joint, a multi-link section, and a continuously-flexible section.

3. The system of claim 1, wherein the linkage is compliant and stretches under a regulated value of the actuator force by an amount corresponding to more than a permitted inaccuracy in joint articulation.

4. The system of claim 1, wherein the control system regulates the actuator force transmitted to the linkage to be independent of a position of the actuator.

5. The system of claim 1, wherein the control system determines the actuator force using a function for which the actuator force varies between a minimum value and a maximum value.

6. The system of claim 5, wherein the minimum value keeps the linkage in tension.

7. The system of claim 5, wherein across a range of variation of the function, the actuator force varies with a difference between a current position measurement of the joint and a current desired position of the joint.

8. The system of claim 5, wherein the force varies linearly with a difference between the current position measurement and the current desired position.

9. The system of claim 5, wherein across a range of variation, the actuator force varies with a difference between a velocity of the joint and a current desired velocity of the joint.

10. The system of claim 9, wherein the actuator force varies linearly with the difference between the velocity of the joint and the current desired velocity of the joint.

11. The system of claim 5, wherein across the range of variation, the actuator force depends on a current velocity of the actuator.

12. The system of claim 1, further comprising:
a second actuator; and
a second linkage having a first end attached to the joint and a second end mechanically coupled to the second actuator to allow the transmission of a second force for articulation of the joint, and wherein
across a range of variation of a second actuator force that the second actuator applies to the second linkage, the second actuator force depends on a current velocity of the second actuator.

13. The system of claim 12, wherein the control system determines the second actuator force using a function of a difference between current velocities of the actuators associated with the joint.

14. The system of claim 1, wherein the control system determines the actuator force using a function of a difference between a current position measurement of the joint and a current desired position of the joint and a difference between a velocity of the joint and a current desired velocity of the joint.

15. The system of claim 1, wherein the control system determines the actuator force using an integral of differences between the position measurements and desired positions.

16. The system of claim 1, wherein the control system determines the actuator force using a function of a difference between a current desired velocity of the linkage and a current velocity of the linkage computed based on a current actuator velocity.

17. The system of claim 1, wherein the control system regulates the actuator force as a function of the sensed distal positions more than 250 times per second.

18. The system of claim 1, wherein the linkage and the actuator are backdrivable.

19. The system of claim 1, wherein the actuator comprises a direct drive electrical motor.

20. The system of claim 19, wherein the control system regulates the actuator force transmitted to the linkage by controlling a motor current.

21. The system of claim 1, wherein the linkage comprises a tendon including at least one of a polymer tendon, a rod element, and a Bowden cable.

22. The system of claim 1, further comprising:
a second actuator; and
a second linkage having a first end attached to the joint and a second end mechanically coupled to the second actuator to allow the transmission of a force for articulation of the joint.

23. A method for controlling a joint of a medical instrument, the method comprising:
measuring a position of a joint;
receiving a command indicating a desired position of the joint;
determining an actuator force that is independent of a position of the actuator, wherein in determining the actuator force includes using the position of the joint and the desired position of the joint; and
operating an actuator to apply the actuator force to a linkage that is coupled to the joint.

24. The method of claim 23, wherein the linkage has a compliance such that the linkage fails to provide a relationship between positions of the joint and positions of the actuator that is sufficiently accurate for control of the joint using the relationship.

25. The method of claim 23, wherein using the position and the desired position comprises evaluating a function that depends on a difference between the position of the joint and a desired position of the joint and a difference between a velocity of the joint and a desired velocity of the joint.

26. The method of claim 23, further comprising:
determining a velocity of the joint; and
receiving a command indicating a desired velocity of the joint, wherein
determining the actuator force includes using the velocity of the joint and the desired velocity of the joint.

27. The method of claim 23, further comprising:
determining a velocity of the actuator; and
receiving a command indicating a desired velocity of the joint, wherein
determining the actuator force includes using the velocity of the actuator and the desired velocity of the joint.

28. The method of claim 23, further comprising:
determining a first velocity of the actuator; and
determining a second velocity of a second actuator that is coupled to the joint through a second linkage, wherein
determining the actuator force includes using a difference between the first and second velocities.

29. The method of claim 23, further comprising summing differences between the position measurements and desired positions to determine an accumulated difference, wherein determining the actuator force includes using the accumulated difference.

* * * * *